United States Patent [19]

Wiley et al.

[11] 4,064,341
[45] Dec. 20, 1977

[54] NOGALAMYCINIC ACID AND DERIVATIVES THEREOF

[75] Inventors: Paul F. Wiley; Jian L. Johnson, both of Kalamazoo, Mich.

[73] Assignee: The Upjohn Company, Kalamazoo, Mich.

[21] Appl. No.: 748,718

[22] Filed: Dec. 9, 1976

[51] Int. Cl.$^2$ ............................................. C07H 15/26
[52] U.S. Cl. ..................................... 536/17; 424/180; 536/4
[58] Field of Search ................................. 536/4, 17

[56] References Cited

U.S. PATENT DOCUMENTS

| 3,183,157 | 5/1965 | Bhuyan et al. | 424/120 |
| 3,501,569 | 3/1970 | Wiley et al. | 424/119 |
| 3,686,238 | 8/1972 | Zaffaroni | 536/17 |
| 3,976,667 | 8/1976 | Kelly | 536/17 |

Primary Examiner—Johnnie R. Brown
Attorney, Agent, or Firm—Roman Saliwanchik

[57] ABSTRACT

Novel antibiotic, nogalamycinic acid (U-51,205) prepared by the chemical modification of the known antibiotic nogalamycin. Nogalamycinic acid is active against various microorganisms, for example, *Mycobacterium avium, Bacillus subtilis, Lactobacillus casei, Staphylococcus aureus,* and *Sarcina lutea.* Thus, nogalamycinic acid can be used to inhibit the growth of the above microorganisms in various environments.

2 Claims, No Drawings

NOGALAMYCINIC ACID AND DERIVATIVES THEREOF

The invention described herein was made in the course of, or under Contract NO1-CM-43753 with the National Cancer Institute, National Institutes of Health, Bethesda, Maryland 20014.

BACKGROUND OF THE INVENTION

The known antibiotic nogalamycin, and a process for its preparation, are described in U.S. Pat. No. 3,183,157. The structure of nogalamycin can be shown as follows:

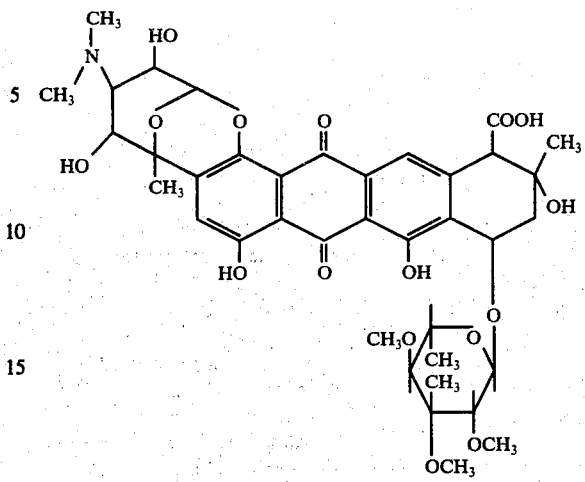

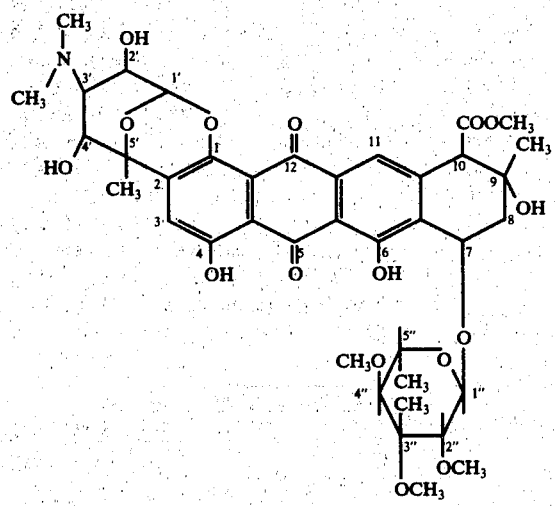

Antibiotics nogalarol and nogalarene, produced by acid hydrolysis of nogalamycin, and o-methylnogalarol, produced by acidic methanolysis of nogalamycin or nogalarol, are disclosed in U.S. Pat. No. 3,501,569.

BRIEF SUMMARY OF THE INVENTION

Nogalamycinic acid can be prepared by chemical modification of nogalamycin. This modification is accomplished by the use of a strong base, for example, NaOH. Nogalamycinic acid is biologically active, as disclosed above, and can be used in various environments to inhibit the growth of susceptible microorganisms. For example, nogalamycinic acid can be used for treating breeding places of silkworms, to prevent or minimize infections which are well known to be caused by *Bacillus subtilis*. Further, nogalamycinic acid can be used to control *Mycobacterium avium* which is a known producer of generalized tuberculosis in birds and rabbits.

DETAILED DESCRIPTION OF THE INVENTION

Nogalamycinic acid can be shown by the following structure:

Nogalamycinic acid can be prepared by base hydrolysis of nogalamycin. The hydrolysis can be conducted with a base ranging from about 0.2 to about 2.0 N. Examples of bases which can be used are NaOH, Ca(OH)$_2$, and Ba(OH)$_2$.

The reaction can be conducted at a temperature of about 5° C. to about 40° C.

Nogalamycinic acid can be acylated under standard acylating conditions with an appropriate acid halide or anhydride to give the acylated compounds. The acylation is carried out in the presence of an acid-binding agent. Suitable acid-binding agents include: amines such as pyridine, quinoline, and isoquinoline, and buffer salts such as sodium acetate. The preferred base is pyridine. Carboxylic acids suitable for acylation include (a) saturated or unsaturated, straight or branched chain aliphatic carboxylic acids, for example, acetic, propionic, butyric, isobutyric, tertbutylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like; (b) saturated or unsaturated, alicyclic carboxylic acids, for example, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexaneacetic acid, cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutylbenzoic acid, and the like; and (e) aromatic aliphatic carboxylic acids, for example, phenylacetic acid, phenylpropionic acid, phenylvaleric acid, cinnamic acid, phenylpropiolic acid, and naphthylacetic acid, and the like. Also, suitable halo-, nitro-, amino-, cyano-, and lower alkoxy- hydrocarbon carboxylic acids include hydrocarboncarboxylic acids as given above which are substituted by one or more of halogen, nitro, amino, cyano, or lower alkoxy, advantageously lower alkoxy of not more than six carbon atoms, for example, methoxy, ethoxy, propoxy, butoxy, amyloxy, hexyloxy groups and isomeric forms thereof. Examples of such substituted hydrocarbon carboxylic acids are: mono-, di-, and trichloroacetic acid;

α- and β-chloropropionic acid;
α- and γ-bromobutyric acid;
α- and δ-iodovaleric acid;
mevalonic acid;
2- and 4-chlorocyclohexanecarboxylic acid;
shikimic acid;
2-nitro-1-methyl-cyclobutanecarboxylic acid;
1,2,3,4,5,6-hexachlorocyclohexanecarboxylic acid;
3-bromo-2-methylcyclohexanecarboxylic acid;
4- and 5-bromo-2-methylcyclohexanecarboxylic acid;
5- and 6-bromo-2-methylcyclohexanecarboxylic acid;
2,3-dibromo-2-methylcyclohexanecarboxylic acid;
2,5-dibromo-2-methylcyclohexanecarboxylic acid;
4,5-dibromo-2-methylcyclohexanecarboxylic acid;
5,6-dibromo-2-methylcyclohexanecarboxylic acid;
3-bromo-3-methylcyclohexanecarboxylic acid;
6-bromo-3-methylcyclohexanecarboxylic acid;
1,6-dibromo-3-methylcyclohexanecarboxylic acid;
2-bromo-4-methylcyclohexanecarboxylic acid;
1,2-dibromo-4-methylcyclohexanecarboxylic acid;
3-bromo-2,2,3-trimethylcyclopentanecarboxylic acid;
1-bromo-3,5-dimethylcyclohexanecarboxylic acid;
homogentisic acid, o-, m-, and p-chlorobenzoic acid;
anisic acid;
veratric acid;
trimethoxybenzoic acid;
trimethoxycinnamic acid;
4,4'-dichlorobenzilic acid;
o-, m-, and p-nitrobenzoic acid;
cyanoacetic acid;
3,4- and 3,5-dinitrobenzoic acid;
2,4,6-trinitrobenzoic acid;
cyanopropionic acid;
ethoxyformic acid (ethyl hydrogen carbonate);
and the like.

The acylated compound, as described above, can be used in animals for the same biological purposes as disclosed above for nogalamycinic acid. For example, the acylated compound can be given in oral form to an animal possessing the necessary enzyme to remove the acyl group, thus freeing the parent antibiotic compound which then inhibits susceptible bacteria.

Nogalamycinic acid forms salts with non-toxic alkali metals and alkaline earth metals. Metal salts can be prepared by dissolving nogalamycinic acid in methanol, adding a dilute metal base until the pH of the solution is about 9 to 11, and freeze drying the solution to provide a dried residue consisting of the metal salt. Metal salts can be, for example, the sodium, potassium, and calcium salts.

Nogalamycinic acid salts, as described above, can be used for the same antibacterial purposes as nogalamycinic acid.

Nogalamycinic acid has demonstrated antitumor activity against L1210 in vitro, and against P388 in vivo in mice.

The following examples are illustrative of the process and products of the invention, but are not to be construed as limiting. All percentages are by weight and all solvent mixture proportions are by volume unless otherwise noted.

EXAMPLE 1

Nogalamycinic Acid

Forty grams (0.05 mole) of nogalamycin was dissolved in 356 ml of 1 N KOH (0.36 mole), and 310 ml of water was added. The solution was stirred overnight at room temperature. The reaction mixture was acidified to pH 3.0 by adding 30% $H_2SO_4$ dropwise with stirring. The precipitate was collected by centrifugation and the precipitate was washed three times with water. The dried product weighed 28.5 g. Ten grams was dissolved in 125 ml of methanol and put on 500 g of silica packed in $CHCl_3$—MeOH (95:5). This was developed with $CHCl_3$—MeOH (95:5) increasing gradually to $CHCl_3$—MeOH (4:1). Elution was continued with $CHCl_3$—MeOH (1:1) until nogalamycinic acid had been eluted as determined by thin layer chromatography (tlc) using $CHCl_3$—MeOH—$H_2O$ (78:20:2). Evaporation in vacuo of the fractions containing chromatographically pure material gave a red solid, wt. 2.3 g; mp 219°–229° C.; Rf (tlc, $CHCl_3$—MeOH—$H_2O$; 78:20:2) 0.25; $\alpha_D$ +456° (C 0.37, $CH_3OH$); uv (EtOH) λmax nm 236 (ε 39,950), 269 (ε 21,350), 291 sh (ε 8,700), 482 (13,550); ir (Nujol) 3450, 1670, 1630, 1595, 1580, 1290, 1230, 1215, 1135, 1095, 1060, 1015, 980, 920, 855, 830, 780, 763 and 725 $cm^{-1}$; mass spectrum m/e 729 (M+ —$CO_2$); $^1$H NMR ($CDCl_3$—$CD_3OD$) δ 1.38 (m, 9 H, 3 $CH_3C$), δ 1.80 (s. 3 H, $CH_3C$), δ 3.15 (s, 6H, $(CH_3)_2NH^+$), δ 3.38, 3.40, 3.68 (3 s, 9 H, 3 $CH_3O$), δ 3.2–4.0 (m, CHO and CHN), δ 5.24 (d, 1 H, anomeric), δ 5.88 (d, 1 H, anomeric), δ 6.92 (s, 1 H, aromatic) and δ 7.47 (s, 1 H, aromatic); $^{13}$C NMR ($CDCl_3$—$CD_2OD$) 16.4, 19.3, 24.6, 31.5 (4 $CH_3C$), δ 42.5 [$(CH_3)_2N$], δ 49.9, 58.2, 60.3, 62.5, 67.8, 68.5, 70.6, 71.6, 74.0, 77.3, 79.6, 82.1 and 85.9 ($CH_3O$, CHO and CHN), δ 97.3 and 100.2 (anomeric), δ 113.1, 114.1, 116.0, 120.7, 125.8, 131.0, 132.5, 137.2, 147.4, 147.8, 156.0 and 161.4 (aromatic), δ 178.9, 181.6 and 191.4 (carbonyl).

| Antimicrobial Activities Of Nogalamycinic Acid | |
|---|---|
| Organism | Zone Size (mm) |
| Saccharomyces pastorianus | 0 |
| Mycobacterium avium | 23 |
| Klebsiella pneumoniae | 0 |
| Bacillus subtilis | 28 |
| Lactobacillus casei | 34 |
| Staphylococcus aureus | 17 |
| Proteus vulgaris | 0 |
| Escherichia coli | 0 |
| Salmonella schottmuelleri | 0 |
| Sarcina lutea | 24 |

The above antimicrobial tests were run by dipping 13 mm filter paper discs into a 1 mg/ml solution of the test substance in methanol (uptake about 20 microliters/disc) and placing the discs on agar plates containing a 1.3 mm layer of agar freshly seeded with the test organism. Discs dipped in methanol alone gave no inhibition zones. The agar media used, available from the Difco Company, Detroit, Michigan, were as follows: for *B. subtilis* and *K. pneumoniae*, Streptomycin agar; for *S. lutea*, Penassay agar; for *L. casei*, thioglycollate agar; for *S. aureus, P. vulgaris, E. coli, S. schottmuelleri*, nutrient agar; for *M. avium*, Brain Heart Infusion agar; and, for *S. pastorianus*, Gray's medium which has the following ingredients:

| | Gm/liter $H_2O$ |
|---|---|
| Glucose | 30 |
| Yeast Extract | 7 |
| $KH_2PO_4$ | 5 |
| Agar | 15 |

The plates were incubated 18 to 24 hours at 37° C., except for those containing *S. lutea* which were incubated at 32° C., before reading the zones.

It is claimed:

1. Nogalamycinic acid, a compound having the following structure:

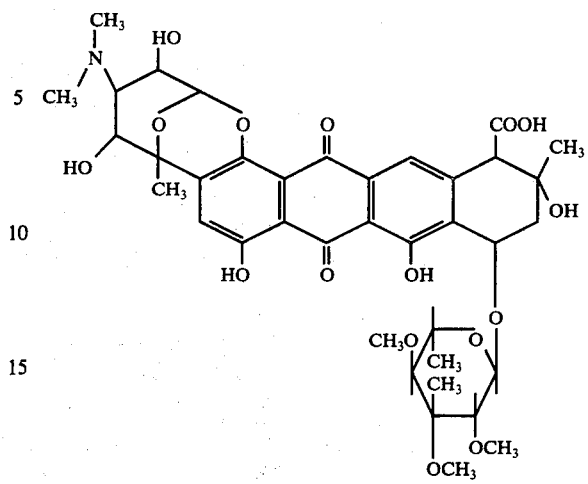

and non-toxic alkali and alkaline earth metal salts thereof.

2. Acylates of nogalamycinic acid wherein said acyl group consists of hydrocarbon carboxylic acid acyl of from 2 to 18 carbon atoms, inclusive; halo-, nitro-, amino-, cyano-, and lower alkoxy-substituted hydrocarbon carboxylic acid acyl of from 2 to 18 carbon atoms, inclusive.

* * * * *